US00PP23589P2

(12) United States Plant Patent
Giesen

(10) Patent No.: US PP23,589 P2
(45) Date of Patent: May 7, 2013

(54) ***DIASCIA* PLANT NAMED 'DALA TRIWHI'**

(50) Latin Name: *Diascia barbarae*
Varietal Denomination: Dala Triwhi

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 436 days.

(21) Appl. No.: 12/924,427

(22) Filed: Sep. 27, 2010

(51) Int. Cl.
*A01H 5/00* (2006.01)

(52) U.S. Cl. ..... Plt./425

(58) Field of Classification Search ..... Plt./425
See application file for complete search history.

*Primary Examiner* — Susan McCormick Ewoldt
(74) *Attorney, Agent, or Firm* — Joshua L. Price

(57) ABSTRACT

A new *Diascia* plant named 'Dala Triwhi' particularly distinguished by the white flowers with medium to darker green foliage; excellent floriferousness and a dense upright habit; has superb heat tolerance and garden performance.

1 Drawing Sheet

Latin name of the genus and species of the plant claimed: *Diascia barbarae.*

Varietal denomination: 'Data Triwhi'.

BACKGROUND OF THE NEW PLANT

The present invention comprises a new *Diascia*, botanically known as *Diascia barberae*, and hereinafter referred to by the variety name 'Dala Triwhi'.

'Data Triwhi' is a product of a planned breeding program. The new cultivar has white flowers with medium to darker green foliage; excellent floriferousness and a dense upright habit; has superb heat tolerance and garden performance.

'Data Triwhi' originated from a hybridization made in June 2005 in a controlled breeding environment in Andijk, Netherlands. The female parent was the unpatented, proprietary plant designated 'DS05-95-1', with smaller flowers, lighter green foliage and shorter stems, with a more compact plant habit.

The male parent of 'Data Triwhi' was an unpatented proprietary plant identified as 'DS03-112-3' with larger flowers, longer and thinner stems. The resultant seed was sown in October 2005.

'Data Triwhi' was selected as one flowering plant within the progeny of the stated cross January 2006 in a controlled environment in Andijk, Netherlands.

The first act of asexual reproduction of 'Data Triwhi' was accomplished when vegetative cuttings were propagated from the initial selection in January 2006 in a controlled environment in Andijk, Netherlands.

BRIEF SUMMARY OF INVENTION

Horticultural examination of plants grown from cuttings of the plant initiated in January 2006, and continuing thereafter, has demonstrated that the combination of characteristics as herein disclosed for 'Dala Triwhi' are firmly fixed and are retained through successive generations of asexual reproduction.

'Dala Triwhi' has not been observed under all possible environmental conditions. The phenotype may vary significantly with variations in environment such as temperature, light intensity and day length.

Plant Breeder's Rights for this cultivar were applied for in Canada on Feb. 18, 2010 (10-6847) and in CVPO on Mar. 5, 2010 (2010/0548). 'Dala Triwhi' has not been made publicly available more than one year prior to the filing of this application.

The following traits have been repeatedly observed and are determined to be basic characteristics of the new variety. The combination of these characteristics distinguishes this *Diascia* as a new and distinct variety.

BRIEF DESCRIPTION OF THE PHOTOGRAPHS

The accompanying photographic drawing shows typical flower and foliage characteristics of 'Dala Triwhi' with colors being as true as possible with an illustration of this type. The photographic drawing shows 3 flowering potted plants of the new variety and a close-up of the flowers.

DETAILED BOTANICAL DESCRIPTION

The aforementioned photographs were taken in April 2010 of plants growing in a greenhouse trial in Gilroy, Calif. USA. These plants were growing in 8 inch basket pots and were approximately 15-16 weeks of age.

The plant descriptions and measurements were taken in mid July 2010 in Andijk, Netherlands. The plants were grown for 8 weeks in a greenhouse trial and then planted outdoors in window boxes with 5 plants in each box.

Color references are made to The Royal Horticultural Society Colour Chart (R.H.S.) 2001.

TABLE 1

DIFFERENCES BETWEEN THE NEW VARIETY 'DALA TRIWHI' AND A SIMILAR VARIETY

| | 'Dala Triwhi' | 'Balwinwite' (U.S. Plant Pat. No. 17,176) |
|---|---|---|
| Foliage color: | Darker green | Lighter green |
| Stem length: | Longer | Shorter |
| Plant habit: | More trailing/larger size | Less trailing/smaller size |

Plant:
*Form, growth and habit*.—Initially compact, rounded and mounded; then becoming a little somewhat trailing; freely branching terminal pinching enhances branching habit.
*Plant height*.—16 cm.
*Plant height* (*inflorescence included*).—25 cm.
*Plant width*.—55 cm.
Roots:
*Number of days to initiate and develop roots*.—16-20 days at about 22 degrees C.
*Type*.—Fine, fibrous, free branching.
*Color*.—RHS N155B but whiter.
Foliage:
*Arrangement*.—Simple; decussate.
*Immature, leaf color, upper surface*.—RHS 139A.
*Lower surface*.—RHS 139B.
*Mature, leaf color, upper surface*.—RHS 139A.
*Lower surface*.—RHS 139B.
*Length*.—2.6 cm.
*Width*.—2.1 cm.
*Shape*.—Cordate.
*Base shape*.—Subcordate.
*Apex shape*.—Obtuse.
*Margin*.—Weakly crenate.
*Texture, upper surface*.—Shiny and glabrous.
*Lower surface*.—Glabrous.
*Color of veins, upper surface*.—RHS 139A.
*Color of veins, lower surface*.—RHS 139A.
*Petiole color*.—RHS 141B.
*Length*.—0.2 cm.
*Diameter*.—0.1 cm.
*Texture*.—Glabrous.
Stem:
*Quantity of main branches*.—25-35.
*Color of stem*.—RHS 137C.
*Length of stem*.—23-25 cm.
*Diameter*.—0.3-0.4 cm.
*Length of internodes*.—2.5-3.0 cm.
*Texture*.—Glabrous.
*Color of raceme*.—RHS 137C.
*Length of raceme*.—12-14 cm.
*Diameter of raceme*.—0.1-0.15 cm.
*Texture*.—Glabrous.
*Pedicel color*.—RHS 141C.
*Pedicel length*.—0.6-1.2 cm.
*Pedicel diameter*.—0.05 cm.
*Pedicel texture*.—Weakly and finely pubescent.
Inflorescence:
*Type*.—Terminal raceme with flowers in an alternate arrangement.
*Blooming habit*.—Flowering freely and continuously from the spring into the fall.
*Quantity of inflorescences per plant*.—70-90 in various stages.
*Quantity of inflorescences raceme*.—About 27 flowers and buds in various development.
*Lastingness of individual blooms on the plant*.—3-4 days depending on weather conditions and temperatures.
*Fragrance*.—None.
Bud (when first opening/showing color):
*Color*.—RHS 155A.
*Length*.—0.4 cm.
*Width*.—0.6 cm.
*Shape*.—Conical.
Immature flower:
*Diameter*.—4.5 cm.
*Color, upper surface*.—RHS N155C.
*Lower surface*.—RHS N155C.
Mature flower:
*Hortizontal diameter*.—1.6-1.8 cm.
*Vertical height*.—1.3-1.5 cm.
*Depth*.—0.3-0.4 cm.
*Color, upper side*.—RHS 155D.
*Underside*.—RHS N155C.
*Corolla tube color inside*.—RHS 13A.
*Outside*.—RHS 11B.
*Corolla tube length*.—0.2 cm.
*Corolla texture, outside*.—Glabrous.
*All lobes, apex*.—Rounded.
*Base*.—Fused.
*Margin*.—Entire.
*Texture*.—Glabrous.
*Upper lobes, size, length*.—0.3 cm.
*Width*.—0.5 cm.
*Lateral lobes, length*.—0.4 cm.
*Width*.—0.6 cm.
*Lower lobes, length*.—0.8-1.0 cm.
*Width*.—1-1.2 cm.
*Spur, color*.—RHS 158D.
*Length*.—0.5 cm.
*Width*.—0.15 cm at the widest point.
*Curvature*.—Strongly bending downwards (approximately 90 degrees).
Calyx: Star-shaped with (5) sepal lobes slanting downward.
*Sepal color*.—RHS 138D.
*Sepal length*.—0.15 cm.
*Sepal width*.—0.1 cm.
*Sepal shape*.—Lanceolate.
*Sepal apex*.—Acute.
*Sepal texture*.—Glabrous.
*Sepal anthocyanin*.—None.
Reproductive organs:
*Stamens*.—4; arching towards and somewhat twisting around the pistil.
*Filament color*.—RHS 145C.
*Filament length*.—0.3 cm.
*Filament diameter*.—0.1 cm.
*Anther color*.—RHS 18A.
*Anther length*.—0.1 cm.
*Pollen color*.—RHS 18A.
*Pollen amount*.—Abundant.
*Pistil*.—1 per flower.
*Pistil length*.—0.4 cm.
*Style color*.—RHS 145C.
*Style length*.—0.3 cm.
*Stigma color*.—RHS 145B.
*Fertility/seed set*.—Has not been observed on this hybrid.
Disease/pest resistance: Disease/pest resistance has not been observed on this hybrid.

What is claimed is:

1. A new and distinct variety of *Diascia* plant named 'Dala Triwhi' substantially as illustrated and described herein.

* * * * *

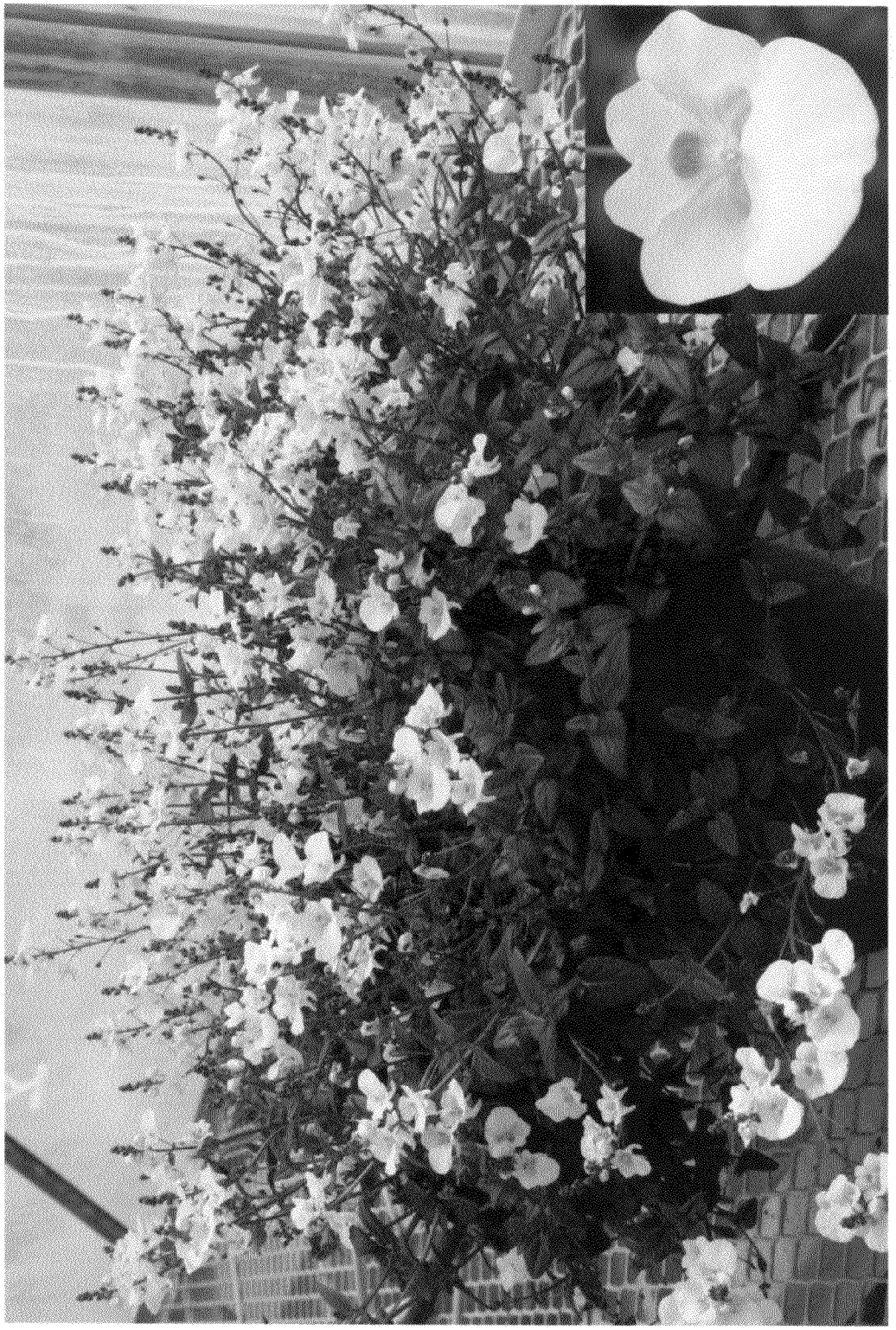

UNITED STATES PATENT AND TRADEMARK OFFICE

CERTIFICATE OF CORRECTION

PATENT NO. : PP23,589 P2
APPLICATION NO. : 12/924427
DATED : May 7, 2013
INVENTOR(S) : Giesen It is certified that error appears in the above-identified patent and that said Letters Patent is hereby corrected as shown below:

Title Page:

At column 1, line 3, delete "'Data Triwhi'" and insert therefor --'Dala Triwhi'--

At column 1, line 10, delete "'Data Triwhi'" and insert therefor --'Dala Triwhi'--

At column 1, line 14, delete "'Data Triwhi'" and insert therefor --'Dala Triwhi'--

At column 1, line 20, delete "'Data Triwhi'" and insert therefor --'Dala Triwhi'--

At column 1, line 24, delete "'Data Triwhi'" and insert therefor --'Dala Triwhi'--

At column 1, line 27, delete "'Data Triwhi'" and insert therefor --'Dala Triwhi'--

Signed and Sealed this
Second Day of July, 2013

Teresa Stanek Rea

Teresa Stanek Rea
*Acting Director of the United States Patent and Trademark Office*